US010583150B2

United States Patent
Lee et al.

(10) Patent No.: US 10,583,150 B2
(45) Date of Patent: Mar. 10, 2020

(54) PHARMACEUTICAL COMPOSITION CONTAINING MTOR INHIBITOR FOR TREATING MACULAR DEGENERATION

(71) Applicants: CUROGENE LIFE SCIENCES CO., LTD., Chungcheongbuk-do (KR); SOONCHUNHYANG UNIVERSITY INDUSTRY ACADEMY COOPERATION FOUNDATION, Chungcheongnam-do (KR)

(72) Inventors: Young-Ill Lee, Chungcheongbuk-do (KR); Steven Hyun Seung Lee, Chungcheongbuk-do (KR); Tae Kwann Park, Seoul (KR)

(73) Assignee: CuroGene Life Sciences Co., Ltd., Chungcheongbuk-Do (KR)

( * ) Notice: Subject to any disclaimer, the term of this patent is extended or adjusted under 35 U.S.C. 154(b) by 0 days.

(21) Appl. No.: 16/327,850

(22) PCT Filed: Mar. 17, 2017

(86) PCT No.: PCT/KR2017/002943
§ 371 (c)(1),
(2) Date: Feb. 24, 2019

(87) PCT Pub. No.: WO2018/048046
PCT Pub. Date: Mar. 15, 2018

(65) Prior Publication Data
US 2019/0192551 A1   Jun. 27, 2019

(30) Foreign Application Priority Data

Sep. 9, 2016 (KR) .......... 10-2016-0116310
Mar. 17, 2017 (KR) .......... 10-2017-0033986

(51) Int. Cl.
*A61K 48/00* (2006.01)
*C07H 21/02* (2006.01)
*A61K 31/7105* (2006.01)
*C12N 15/113* (2010.01)
*C12N 15/86* (2006.01)
*A61P 27/02* (2006.01)

(52) U.S. Cl.
CPC .......... *A61K 31/7105* (2013.01); *A61K 48/00* (2013.01); *A61K 48/0075* (2013.01); *A61P 27/02* (2018.01); *C12N 15/113* (2013.01); *C12N 15/1137* (2013.01); *C12N 15/86* (2013.01); *A01K 2227/105* (2013.01); *A01K 2267/03* (2013.01); *C12N 2310/14* (2013.01); *C12N 2750/14143* (2013.01); *C12Y 207/01001* (2013.01)

(58) Field of Classification Search
CPC .. C12N 2310/11; C12N 15/115; A61K 31/713
See application file for complete search history.

(56) References Cited

U.S. PATENT DOCUMENTS

2012/0114637 A1    5/2012  Nivaggioli et al.
2015/0366876 A1 * 12/2015  Lakkaraju .............. A61K 45/06
                                                    514/217

FOREIGN PATENT DOCUMENTS

| WO | WO2009143371 A2 | 11/2009 | |
|----|-----------------|---------|---|
| WO | WO2010064851 A2 | 6/2010 | |
| WO | WO 2010/064851 A2 * | 10/2010 | ........... C12N 15/115 |
| WO | WO2013056105 A2 | 4/2013 | |

OTHER PUBLICATIONS

Zhao et al. (Aging, Apr. 2011, vol. 3 No. 4, pp. 346-347).*
Liegl et al. (PLOS One, 2014, vol. 9, Issue 2, e88203, pp. 1-10).*
Johnson, S.C., et al., "mTOR is a Key Modulator of Ageing and Age-Related Disease", "Nature", Jan. 17, 2013, pp. 338-345, vol. 493.
Lee, S.H., et al., "Laser Photocoagulation Induces Transduction of Retinal Pigment Epithelial Cells by Intravitreally Administered Adeno-Associated Viral Vectors", "Human Gene Therapy Methods", 2015, pp. 159-161, vol. 26, No. 5.
Milligan, J.F., et al., "Synthesis of Small RNAs Using T7 RNA Polymerase", "Methods in Enzymology", 1989, pp. 51-62, vol. 180.
Verma, S., et al., "Modified Oligonucleotides: Synthesis and Strategy for Users", "Annu. Rev. Biochem.", 1998, pp. 99-134, vol. 67.

* cited by examiner

*Primary Examiner* — Amy H Bowman
(74) *Attorney, Agent, or Firm* — Hultquist, PLLC; Steven J. Hultquist

(57) ABSTRACT

The present invention relates to a pharmaceutical composition for treating macular degeneration, and more particularly to a pharmaceutical composition for treating macular degeneration, which comprises an inhibitor of mTOR gene expression. The pharmaceutical composition according to the present invention can effectively treat age-related macular degeneration, a representative retinal disease that causes blindness in adults.

2 Claims, 6 Drawing Sheets
(4 of 6 Drawing Sheet(s) Filed in Color)
Specification includes a Sequence Listing.

(a)

(b)

(a)

(b)

(c)

PHARMACEUTICAL COMPOSITION CONTAINING MTOR INHIBITOR FOR TREATING MACULAR DEGENERATION

CROSS-REFERENCE TO RELATED APPLICATIONS

This application is a U.S. national phase under the provisions of 35 U.S.C. § 371 of International Patent Application No. PCT/KR17/02943 filed Mar. 17, 2017, which in turn claims priority of Korean Patent Application No. 10-2016-0116310 filed Sep. 9, 2016 and Korean Patent Application No. 10-2017-0033986 filed Mar. 17, 2017. The disclosures of such International Patent Application No. PCT/KR17/02943, Korean Patent Application No. 10-2016-0116310, and Korean Patent Application No. 10-2017-0033986 are hereby incorporated herein by reference in their respective entireties, for all purposes.

TECHNICAL FIELD

The present invention relates to a pharmaceutical composition for treating macular degeneration, and more particularly to a pharmaceutical composition for treating macular degeneration, which contains an inhibitor of mTOR gene expression.

BACKGROUND ART

Age-related macular degeneration (AMD) is the most common cause of blindness in people over 65 years in many developed countries. It is known that the underlying causes of this disease are the functional decline and age-related atrophy of the retinal pigment epithelium (RPE). The RPE plays a crucial role in the maintenance of homeostasis and physiological functioning of the retina, while playing a key role in visual function. AMD is also thought to be caused by abnormalities resulting from age-related changes to Bruch's membrane, which functions as the basement membrane of the RPE, as well as the degeneration of the choriocapillaris, which supplies nutrients and oxygen to photoreceptor cells located in the outermost layer of the RPE and the neural retina, wherein phototransduction occurs.

Due to such changes, age-related macular degeneration is phenotypically divided into two subtypes: dry AMD, which is characterized by the degeneration and functional decline of the RPE, Bruch's membrane and the choriocapillaris; and wet AMD, which involves choroidal neovascularization (CNV) in addition to the aspects of dry AMD.

Dry AMD is characterized by the occurrence of drusen, in which complement system proteins and apolipoproteins accumulate between the RPE and the choriocapillaris. Perhaps the presence of drusen interferes with the movement of oxygen and nutrients in the choriocapillaris, and the occurrence of drusen itself reflects a decline in RPE cell function, eventually leading to oxygen deficiency, obstruction of mass transfer, and inflammation due to the death of RPE cells. Thus, dry AMD is characterized by geographic atrophy (GA), which results in extensive defects to RPE tissue over time.

Thus far, no therapeutics have been developed for dry AMD, though it is possible to delay its progression of somewhat via health foods containing vitamins, trace elements, and lutein, an antioxidant. Recently, various clinical studies targeting complement system-related proteins have been conducted, but studies targeting C3, C5, among others, have failed in developing an acceptable therapeutic. Lampalizumab (developed by Roche), a monoclonal antibody developed for factor blockade, was observed for 18 months in a phase II clinical trial, and showed the ability to inhibit GA enlargement by 20% when injected intravitreally once a month. It is currently undergoing phase III studies.

Wet AMD occurs in 5-10% of patients with dry AMD, and exhibits an acute phenotype that can cause blindness within a few months if left untreated, unlike dry AMD where the deterioration of vision progresses over a period of several years or even decades. In this case, a wide range of oxygen partial pressure reduction and nutrient decline across the subretinal space and the sub-RPE space, that is, tissue ischemia and the accompanying inflammatory response, play an important role. Oxidative stress and complement systems also act on wet AMD, with the latter playing an important role in immunological mechanisms, and choroidal neovascularization (CNV) characteristically occurs in the subretinal space or the sub-RPE space, resulting in serous fluid leakage and bleeding.

Choroidal neovascularization is known to be generated by endothelial cells, RPE cells, and inflammatory cells, such as monocytes and macrophages. Treatment of wet AMD utilizes anti-VEGF antibodies, whose use began around 2005, and has been shown to reduce blindness in many patients. The reason for the use of such agents is because it is known that VEGF plays a major role in the development of choroidal neovascularization. However, the use of anti-VEGF antibodies does not completely inhibit the formation and growth of choroidal neovascularization lesions, and photoreceptor cells in the macula which is the central part of the retina where choroidal neovascularization develops, eventually lose their function due to disintegration of the underlying RPE tissue. In addition, even when anti-VEGF antibodies are used, they act only on endothelial cells on the surface of the choroidal neovascularization lesions, and hence the size of choroidal neovascularization lesions continues to increase rather than decrease.

As such, it is necessary to develop drugs that target pathways other than the VEGF pathway involved in the development of choroidal neovascularization. Recently, Novartis has developed a drug having anti-PDGF effects, which serves to enhance the effects of drugs by separating pericytes, which are thought to be a major cause preventing anti-VEGF antibodies from effectively acting on vascular endothelial cells, from endothelial cells of choroidal neovascularization, easing the binding of anti-VEGF antibodies to the endothelial cells.

On the other hand, mTOR (mammalian target of rapamycin) plays an important role in cell proliferation and autophagy, and is considered a potential target in the treatment of malignant tumors. Thus, the development of therapeutic agents targeting mTOR has been conducted by many researchers. These therapeutic agents are mainly used for the purpose of inhibiting the action of mTOR to inhibit cell proliferation and activate autophagy.

Accordingly, the present inventors have made extensive efforts to develop a therapeutic with a novel target and mechanistically separate from the anti-VEGF antibodies currently used to treat macular degeneration, and as a result, have found that when a macular degeneration model elicited via laser-induced choroidal neovascularization is treated with an mTOR inhibitor, the lesion size of macular degeneration is reduced, thereby completing the present invention.

DISCLOSURE OF INVENTION

Technical Problem

It is an object of the present invention to provide a pharmaceutical composition for treating macular degeneration, which has a drug development target with a new mechanism.

Technical Solution

To achieve the above object, the present invention provides a pharmaceutical composition for treating or preventing macular degeneration, which comprising of a siRNA represented by the nucleotide sequence of SEQ ID NO: 1.

The present invention also provides a pharmaceutical composition for treating or preventing macular degeneration, which comprising a recombinant vector comprising an shRNA (shRNA-mTOR) with the ability to inhibit mTOR and represented by the nucleotide sequence of SEQ ID NO: 1.

The present invention also provides a method for treating macular degeneration, comprised of administering to a patient a siRNA represented by the nucleotide sequence of SEQ ID NO: 1.

The present invention also provides a method for treating macular degeneration, comprised of administering to a patient a recombinant vector encoding a shRNA (shRNA-mTOR) with the ability to inhibit mTOR and represented by the nucleotide sequence of SEQ ID NO: 1.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

BEST MODE FOR CARRYING OUT THE INVENTION

In the present invention, it was attempted to treat age-related macular degeneration, which is caused by the functional decline and age-related atrophy of the retinal pigment epithelium (RPE), by a mechanism other than the neovascularization inhibitory mechanism based on the conventional method employing anti-VEGF antibodies. Furthermore, examinations were made of whether inhibiting the action of the mTOR protein, which plays an important role in cell proliferation and autophagy, is effective in the treatment of macular degeneration. As a result, it was found that when a laser-induced choroidal neovascularization macular degeneration animal model was treated with a shRNA-based mTOR inhibitor, the size of the lesion in the treated group significantly decreased.

Therefore, in one aspect, the present invention is directed to a pharmaceutical composition for treating or preventing macular degeneration and is comprised of a siRNA represented by the nucleotide sequence of SEQ ID NO: 1.

The siRNA represented by the nucleotide sequence of SEQ ID NO: 1 is a siRNA acting as an inhibitor of mTOR, and it is thought that the inhibition of mTOR can block the introduction and proliferation of various types of inflammatory cells involved in choroidal neovascularization (CNV) in age-related macular generation (AMD). This blocking is an effect which cannot be exhibited by anti-VEGF antibodies, and may represent a new drug development target with a novel mechanism. The inhibition of mTOR not only inhibits the proliferation of endothelial cells, a major component of choroidal neovascularization, but also activates autophagy. In addition, it inhibits the apoptosis of neural cells present in neural retina tissue.

The sequence of siRNA that is used in the present invention is as follows:

SEQ ID NO: 1: GAAUGUUGACCAAUGCUAU

The shRNA-based mTOR inhibitor used in the present invention was known to mediate autophagy activation in malignant tumor cells at the time of initial development. In the present invention, it has been found that the shRNA-based mTOR inhibitor activates autophagy in lesional and perilesional areas of a macular degeneration animal model.

Figure 1:
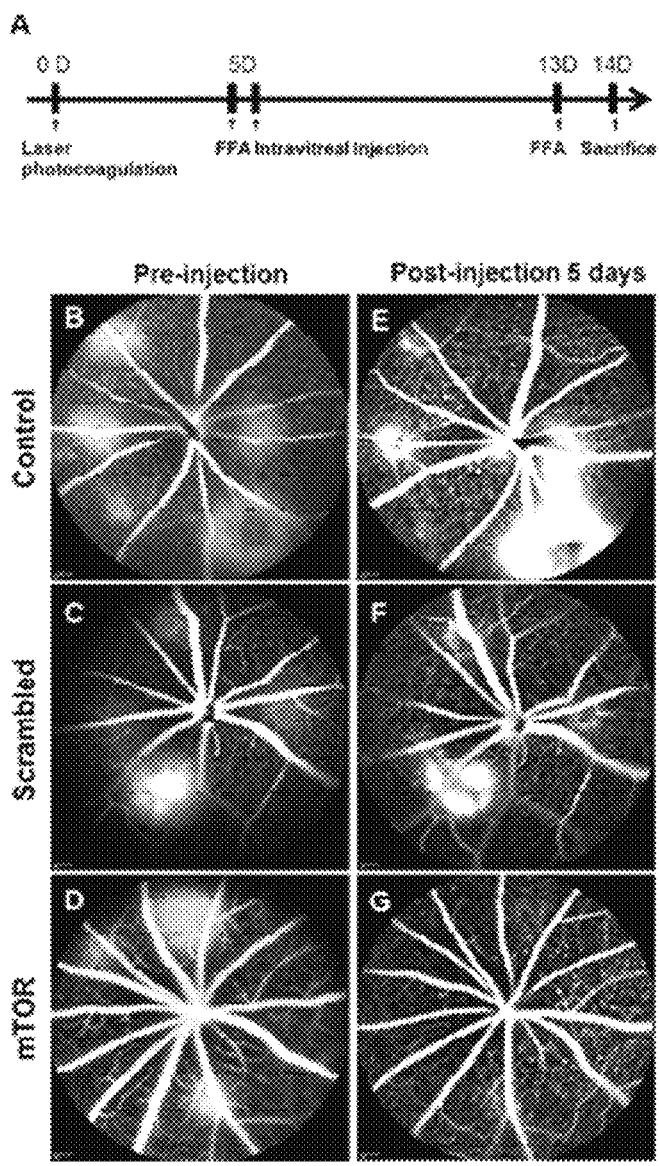
FIG. 1 shows the results of fundus fluorescein angiography (FFA) performed to confirm that fluorescein leakage from choroidal neovascularization was reduced after administering shRNA to a laser-induced choroidal neovascularization macular degeneration model. Specifically, A shows the experimental schematic, which consists of induction of macular degeneration, administration of shRNA, and fundus fluorescein angiography; B to D show the results of fundus fluorescein angiography before administration of shRNA; and E to G show the results of fundus fluorescein angiography after administration of shRNA.
Figure 3:
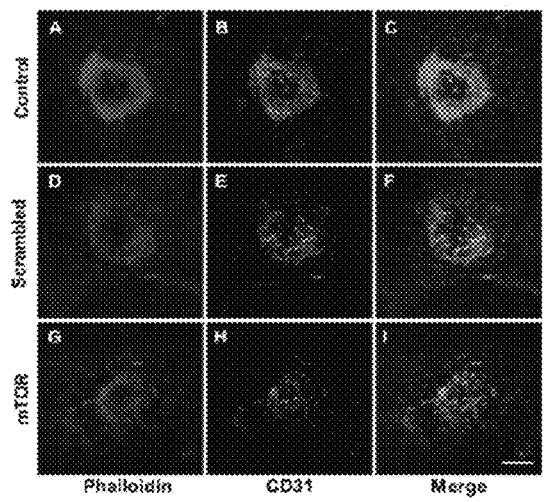
FIG. 3 shows the results of analyzing changes in the expression of CD31 after administering shRNA to a laser-induced choroidal neovascularization macular degeneration model. Specifically, (a) shows images from retinal pigment epithelium-choroid complex tissue samples; (b) is its corresponding graph; and (c) shows images of neural retina-retinal pigment epithelium-choroid complex tissue samples.
Figure 3:
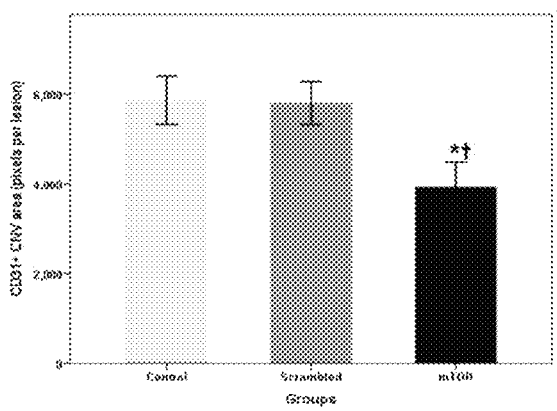
Figure 3:
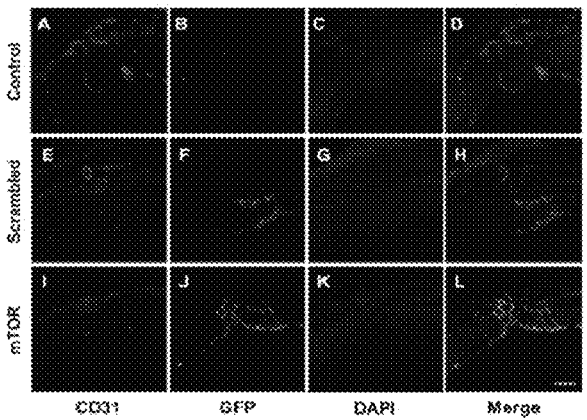

In one example of the present invention, an experiment was performed in laser-induced choroidal neovascularization macular degeneration animal models, and it was confirmed that the size of lesion in the group treated with mTOR shRNA was significantly reduced when compared to an untreated saline control group and a non-specific shRNA control group, indicating that the mTOR shRNA has a therapeutic effect against macular degeneration (FIGS. 1 and 3).

Figure 4:
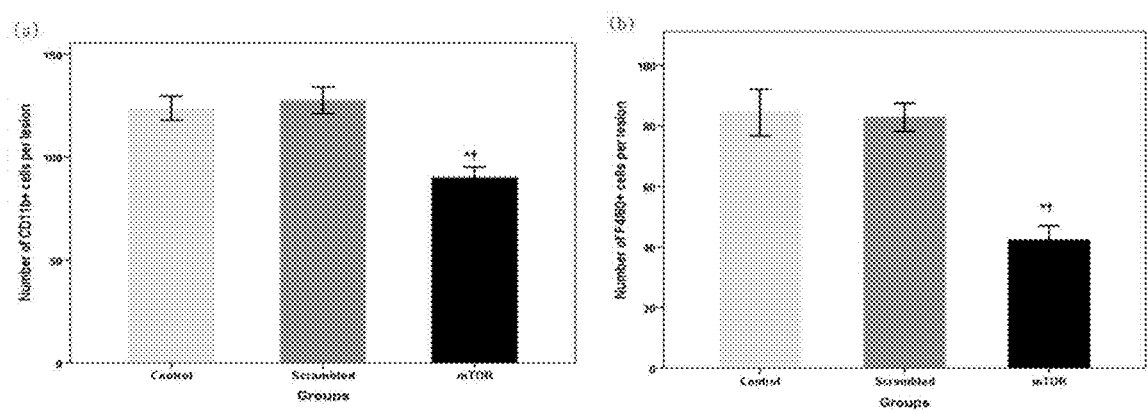
FIG. 4 depicts graphs showing the results of examining changes in inflammatory cells after administration of shRNA to a laser-induced choroidal neovascularization macular degeneration model wherein (a) shows CD11b-positive cells and (b) shows F4/80-positive cells.
Figure 6:
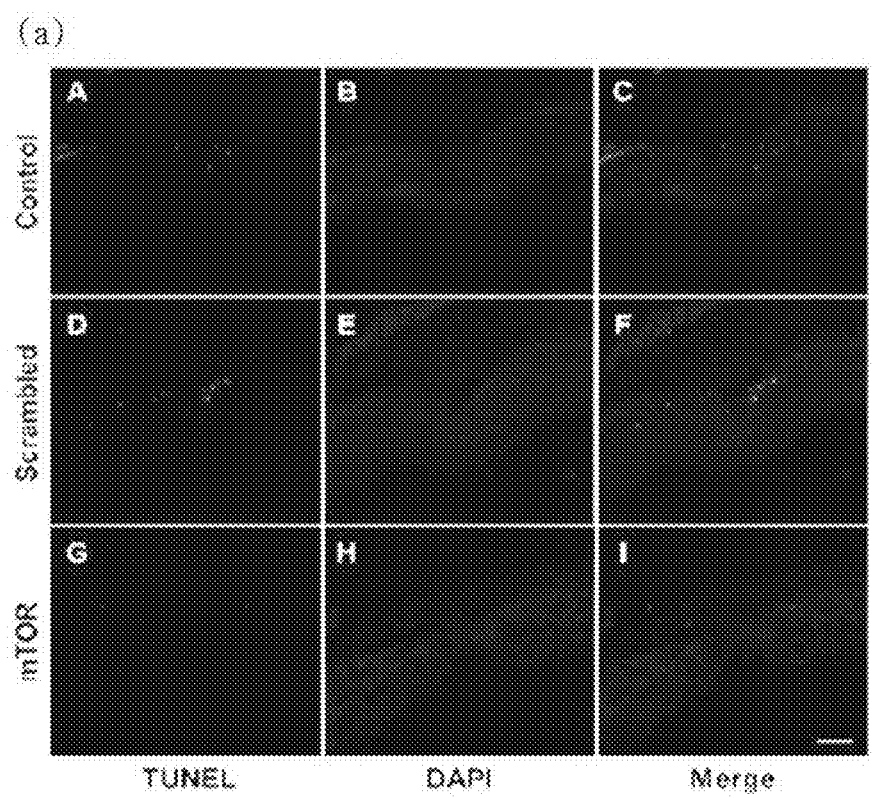
FIG. 6 depicts images (a) and a graph (b), which show the results of examining changes in apoptosis after administering shRNA to a laser-induced choroidal neovascularization macular degeneration model.
Figure 6:
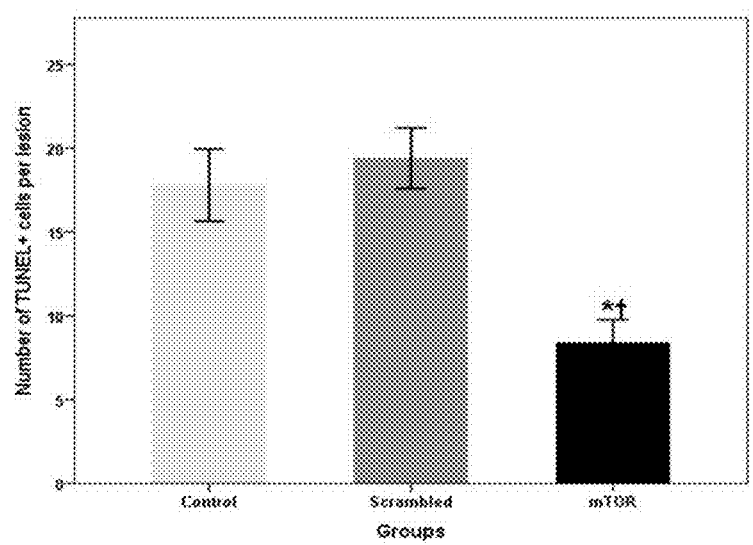

In another example of the present invention, it was confirmed that the number of inflammatory cells around a choroidal neovascularization lesion administered with mTOR shRNA was reduced and the apoptosis of neural cells around the lesion was also reduced. This suggests that the shRNA-based inhibition of mTOR reduces the size of choroidal neovascularization lesions, and also exhibits the effects of alleviating inflammatory responses and inhibiting the apoptosis of neural cells in peripheral neural retinal tissue (FIGS. 4 and 6).

The siRNA that is used in the present invention may be prepared according to RNA molecule preparation methods known in the art. The RNA molecule preparation methods include chemical synthesis methods and enzymatic methods. For example, chemical synthesis of an RNA molecule may be performed using the method disclosed in the literature (Verma and Eckstein, Annu. Rev. Biochem. 67, 99-134, 1999), and enzymatic synthesis of an RNA molecule may be performed by a method using phage RNA polymerases, such as T7, T3, and SP6 RNA polymerases, as disclosed in the literature (Milligan and Uhlenbeck, Methods Enzymol. 180: 51-62, 1989).

In the present invention, examples of a viral or non-viral vector useful for delivering the siRNA against mTOR include baculoviridae, parvoviridae, picornoviridae, herpesviridae, poxviridae, and adenoviridae, but is not limited thereto.

If the mTOR-targeting siRNA according to the present invention is provided as a pharmaceutical composition, the pharmaceutical composition may further contain a suitable carrier, excipient, or diluent which is commonly used in the preparation of pharmaceutical compositions.

Examples of carriers, excipients, and diluents that can be used in the present invention may include lactose, dextrose, sucrose, sorbitol, mannitol, xylitol, erythritol, maltitol, starch, gum acacia, alginate, gelatin, calcium phosphate, calcium silicate, cellulose, methyl cellulose, microcrystalline cellulose, polyvinylpyrrolidone, water, methylhydroxybenzoate, propylhydroxybenzoate, talc, magnesium stearate, and mineral oil.

The composition can be formulated according to a conventional method. For example, it may be formulated in the form of powders, granules, tablets, capsules, suspensions, emulsions, syrups, aerosols, agents for oral or external applications, suppositories, and sterile injection solutions.

The composition according to the present invention is formulated using diluents or excipients, such as fillers, extenders, binders, wetting agents, disintegrants, or surfactants, which are commonly used. Solid formulations for oral administration include tablets, pills, powders, granules, capsules, etc. Such solid formulations are prepared by mixing the composition of present invention with at least one excipient, such as starch, calcium carbonate, sucrose, lactose, or gelatin.

In addition to simple expedients, lubricants such as magnesium stearate, talc, etc., may also be added. Liquid formulations for oral administration, such as suspensions, internal solutions, emulsions, syrups, etc., may include simple diluents which are commonly used, e.g., water and liquid paraffin, as well as various excipients, e.g., wetting agents, sweeteners, aromatics, preservatives, etc.

Formulations for parenteral administration include sterilized aqueous solutions, non-aqueous solvents, suspensions, emulsions, lyophilized agents, suppositories, etc. Non-aqueous solvents and suspensions may be prepared using propylene glycol, polyethylene glycol, vegetable oils such as olive oil, or injectable esters such as ethyloleate. As a base for suppositories, Witepsol, Macrogol, Tween 61, cacao fat, laurin fat, glycerogelatin, etc. may be used.

The dosage of the composition may vary depending on the patient's age, sex, and weight, but it may be administered at a dosage of 0.1-2.0 mg/kg once or several times a day.

In addition, the preferred dose of such a composition can be suitably selected depending on the route of administration, the severity of disease, the patient's sex, weight, and age, etc. Thus, the dose is not intended to limit the present invention in any way.

The composition may be administered by various routes to mammals, including rats, mice, livestock, and humans. All routes of administration can be contemplated and include, for example, oral, rectal, intravenous, intramuscular, subcutaneous, intrauterine, intrathecal, or intracerebrovascular injections.

In another aspect, the present invention is directed to a pharmaceutical composition for treating or preventing macular degeneration, comprising of a recombinant vector encoding a shRNA (shRNA-mTOR) with the ability to inhibit mTOR and is represented by the nucleotide sequence of SEQ ID NO: 1.

In still another aspect, the present invention is directed to a method for treating macular degeneration, comprised of administering to a patient either a siRNA represented by the nucleotide sequence of SEQ ID NO: 1 or a recombinant vector encoding a shRNA (shRNA-mTOR) with the ability to inhibit mTOR and is represented by the nucleotide sequence of SEQ ID NO: 1.

In the present invention, a viral vector useful for delivering the siRNA against mTOR is most preferably adeno-associated virus (AAV). Adeno-associated viruses are non-immunogenic and non-cytotoxic. In particular, adeno-associated virus serotype 2 can efficiently deliver genes to neural cells of the CNS. In addition, transgenes can be effectively expressed in the neural system.

In the present invention, a non-viral vector useful for delivering the siRNA against mTOR includes all vectors commonly used in genetic therapies, except for the above-described viral vector, and examples thereof include various plasmids and liposomes which may be expressed in eukaryotic cells.

In the meantime, in the present invention, the mTOR-targeting siRNA is preferably linked operably to at least a promoter so that it is suitably transcribed in cells to which it has been delivered. The promoter may be any promoter that can function in eukaryotic cells, but is more preferably a human H1 polymerase-III promoter. For efficient transcription of the mTOR-targeting siRNA, the vector may, if necessary, further comprise regulatory sequences, including a leader sequence, a polyadenylation sequence, a promoter, an enhancer, an upstream activating sequence, a signal peptide sequence, and a transcription termination factor.

EXAMPLES

Hereinafter, the present invention will be described in further detail with references to examples. It will be obvious to a person having ordinary skill in the art that these examples are for illustrative purposes only and are not to be construed to limit the scope of the present invention.

Example 1: Construction of Macular Degeneration Models with Laser-Induced Choroidal Neovascularization (CNV)

To establish age-related macular degeneration animal models, choroidal neovascularization was induced by irradiating a laser to the animal eye. Specifically, 8-week-old male C57/BL6 mice were anesthetized with 40 mg/kg zolazepam/tiletamine and 5 mg/kg xylazine, and then the pupil was dilated with 0.5% tropicamide and 2.5% phenylephrine. To induce choroidal neovascularization (CNV), laser photocoagulation (LP) of the right eye of the mice was induced using a PASCAL diode ophthalmic laser system (Nd:YAG, 532 nm, Topcon Medical Laser Systems, Inc., Santa Clara, Calif., USA). A laser was irradiated to five to six points around the optic nerve head, and then disruption of the Bruch's membrane was confirmed by observing the generation of gaseous bubbles at the laser irradiation points.

As shown in B to D of FIG. 1, induction of choroidal neovascularization could be confirmed by fundus fluorescein angiography 5 days after laser irradiation.

Example 2: Introduction of mTOR shRNA and Confirmation of the Inhibition of mTOR Expression Thereby 2-1: Construction of scAAV Vector and Intravitreal Injection Thereof In this example, a vector derived from scAAV2 (self-complementary adeno-associated virus serotype 2 vector) was used. On 6 days after laser photocoagulation was induced under anesthesia, the pupil of the mouse right eye was dilated and the vector was injected into the vitreous body. Injection of the vector was performed using a NanoFil syringe having a 35 gauge thickness and a blunt end, and 1 µl of the vector was injected at a concentration of $5.0 \times 10^{10}$ viral genomes (vg)/ml. As shown in Table 1 below, the mice with induced choroidal neovascularization were divided into 3 groups, each consisting of 15 animals, and saline, nonspecific shRNA, or the mTOR shRNA of SEQ ID NO: 1 was injected into the vitreous body. Five mice were not subjected to choroidal neovascularization nor intravitreal injection, and were used as a negative control group.

TABLE 1

| Groups | Treatment |
| --- | --- |
| Group 1 (shRNA-mTOR test group) | Laser-induced choroidal neovascularization + AAV-mTOR shRNA/GFP injection |
| Group 2 (shRNA-nonspecific control group) | Laser-induced choroidal neovascularization + AAV-nonspecific shRNA/GFP injection |
| Group 3 (saline control group) | Laser-induced choroidal neovascularization + saline injection |
| Group 4 (negative control group) | Not treated |

2-2: Confirmation of Cells Introduced with scAAV Vector

To determine the type of cells into which the scAAV vector injected into the vitreous body was introduced, a scAAV vector with a GFP-encoding gene inserted therein was used. A frozen section sample was prepared as described in Example 2-3 below, and GFP expression was examined using an anti-GFP antibody (Abcam, Cambridge, Mass.). As a result, it was shown that GFP was expressed not only in inner retinal cells, but also CD31-positive endothelial cells (FIG. 2a). The scAAV vector is known to be introduced into retinal ganglion cells and inner retinal cells, including cells located in the inner nuclear layer in a wild-type mouse retina (Lee S H et al., *Hum Gene Ther Methods* 25:159-61, 2015). However, it was shown that when choroidal neovascularization was induced via laser, the scAAV vector was also introduced into CD31-positive endothelial cells. This suggests that when macular degeneration occurred, it can be treated by targeting endothelial cells using the scAAV vector.

2-3: Preparation of Tissue Samples

The preparation of tissue samples for immunofluorescence staining was performed in the following manner. After anesthetizing animals, 0.1 M PBS containing 150 U/ml heparin was perfused through the heart, and then 4% paraformaldehyde/0.1 M PBS was perfused. The fixed eyeball was dissected, and then the anterior segment containing the cornea and the vitreous body was removed. The neural retina-retinal pigment epithelium-choroid complex tissue samples prepared as described above were additionally fixed in 4% paraformaldehyde/0.1 M PBS. To prepare frozen section samples, the fixed tissues were transferred to and left to stand in 30% sucrose/PBS overnight. Next, the tissues were embedded in OCT compound (Sakura Finetek, Torrance, Calif.), frozen, and sectioned to a thickness of 10 µm. Each of the obtained sagittal sections was attached to a microscope slide.

2-4: Examination of the Inhibition of mTOR Expression by mTOR shRNA

Figure 2:
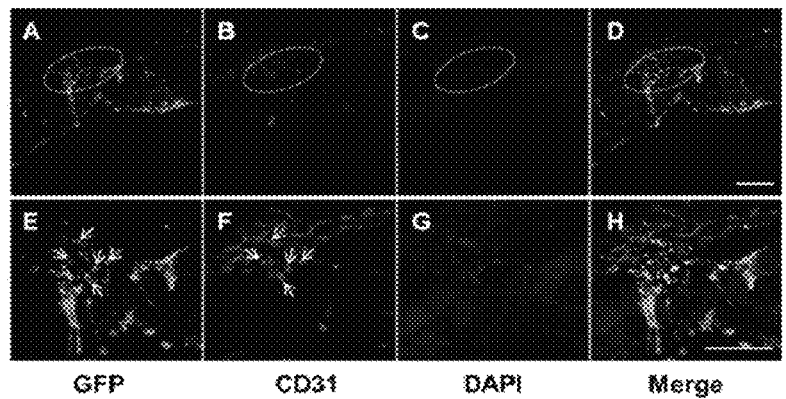
FIG. 2 depicts images showing cells administered with an scAAV vector and changes in the expression of mTOR after intravitreal injection of the scAAV vector. Specifically, (a) shows cells introduced with the vector, and (b) shows changes in the expression of mTOR.
Figure 2:
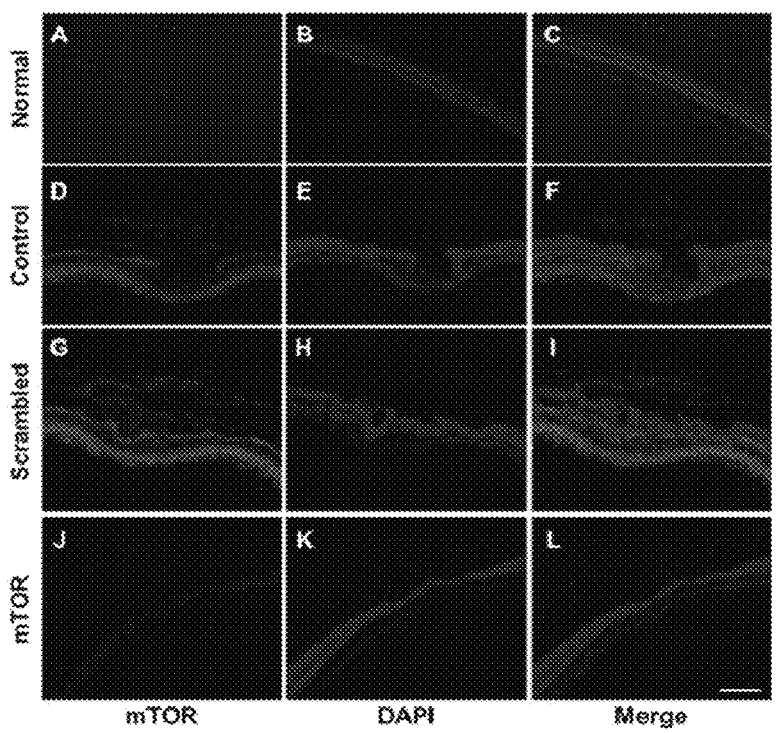

After intravitreal injection with the scAAV vector introduced with the mTOR shRNA of SEQ ID NO: 1, mTOR expression was examined. To examine the expression of mTOR, the frozen section samples prepared as described in Example 2-3 above were fluorescence-stained with an anti-mTOR antibody (1:200; R&D Systems, Minneapolis, Minn., AF15371). As a result, it was confirmed that, in the negative control group not irradiated with a laser, the expression of mTOR was not observed, but in the group with choroidal neovascularization induced by laser irradiation, the expression of mTOR increased in the neural retina and subretinal areas. It was shown that the expression of mTOR was not changed by saline or nonspecific shRNA, but was reduced by the mTOR shRNA, indicating that the above-described sequence is effective in the inhibition of mTOR expression (FIG. 2).

Example 3: Examination of the Therapeutic Effect of mTOR shRNA Against Macular Degeneration In order to examine whether the mTOR shRNA of SEQ ID NO: 1 exhibits a therapeutic effect in macular degeneration animal models, the scAAV vector introduced with the mTOR shRNA as described in Example 2 above was injected intravitreally into macular degeneration animal models, and the therapeutic effect of the shRNA was examined as described in Examples 3-1 to 3-5 below.

3-1: Examination of the Effect of mTOR shRNA on Reduction in Fluorescein Leakage from Choroidal Neovascularization Fluorescein leakage from choroidal neovascularization was measured by fundus fluorescein angiography (FFA). The fundus fluorescein angiography was performed using a scanning laser ophthalmoscope (Heidelberg Retina Angiograph 2; Heidelberg Engineering, Heidelberg, Germany) device. 0.1 ml of 2% fluorescein sodium was injected intraperitoneally into mice under anesthesia, and after 3 to 5 minutes, the pupil was dilated, and then FFA images were acquired. Proper induction of choroidal neovascularization was confirmed 5 days after laser irradiation, and then scAAV-mTOR shRNA was injected intravitreally as described in Example 2-1 above. After 7 days (13 days after laser irradiation), the therapeutic effect was examined. As shown in FIG. 1, in the group treated with saline or non-specific shRNA, there was no change in fluorescein leakage from the lesion area, but in the group treated with the mTOR shRNA, fluorescein leakage was reduced. This suggests that the inhibition of mTOR by the mTOR shRNA is effective in the treatment of macular degeneration.

3-2: Examination of the Inhibition of Blood Vessel Growth by mTOR shRNA

To examine the effect of the mTOR shRNA on the development of choroidal neovascularization, endothelial cells were observed using an anti-CD31 antibody (1:200; BD Pharmingen, Inc., San Diego, Calif., 550274) capable of selectively staining the endothelial cells. The preparation of tissue samples for immunofluorescence staining was performed in the following manner. After anesthetizing animals, 0.1 M PBS containing 150 U/ml heparin was perfused through the heart, and then 4% paraformaldehyde/0.1 M PBS was perfused. The fixed eyeball was dissected, and then the anterior segment containing the cornea and the vitreous body was removed. To prepare retinal pigment epithelium (RPE) tissue samples (RPE whole mounts), the neural retina was additionally removed to make retinal pigment epithelium-choroid complex tissue samples which were then additionally fixed in 4% paraformaldehyde/0.1 M PBS. In addition, to prepare neural retina-retinal pigment epithelium-choroid complex tissue samples, the anterior segment was removed, and the remaining tissue having neural retina attached thereto was additionally fixed in 4% paraformaldehyde/0.1 M PBS. To prepare frozen section samples, the retinal pigment epithelium-choroid complex tissue samples or neural retina-retinal pigment epithelium-choroid complex tissue samples prepared as described above were transferred to and left to stand in 30% sucrose/PBS overnight. Next, the tissues were embedded in OCT compound (Sakura Finetek, Torrance, Calif.), frozen, and sectioned to a thickness of 10 µm. Each of the obtained sagittal sections was attached to a microscope slide.

The retinal pigment epithelium-choroid complex tissue samples were stained with an anti-CD31 antibody and phalloidin (Thermo Fisher Scientific, Waltham, Mass., A22287), and as a result, it was shown that choroidal neovascularization areas were significantly reduced in the group injected with the mTOR shRNA when compared to the groups injected with saline or nonspecific shRNA (FIG. 3). In addition, the results of examining the neural retina-retinal pigment epithelium-choroid complex tissue samples indicated that when the mTOR shRNA was introduced, the number of CD31-positive cells among GFP-expressing cells decreased (FIG. 3).

This suggests that the mTOR shRNA acts on endothelial cells, thereby exhibiting the effects of inhibiting blood vessel growth and treating macular degeneration.

3-3: Examination of Anti-inflammatory Effect of mTOR shRNA

In order to examine whether the alleviation of macular degeneration by inhibition of mTOR is achieved by controlling the activity of inflammatory cells, retinal cross-sections were stained with the anti-CD11b antibody (1:200; Serotec, Oxford, UK, MCA711G) and anti-F4/80 antibody (1:200; Serotec, Oxford, UK, MCA497GA) that selectively stain for leukocytes and macrophages, respectively. For preparation of tissue samples for immunofluorescence staining, neural retina-retinal pigment epithelium-choroid complex tissue samples were prepared as described in Example 3-2 above.

For counting of the number of leukocytes and macrophages, CD11b- and F4/80-positive cells were counted in five retinal cross-sections, respectively. The values were expressed as mean±SEM, and statistical analysis (Kruskal-Wallis test, post-hoc analysis, Bonferroni's method) was performed using SPSS software (ver. 20.0 for Windows; SPSS, Inc., Chicago, Ill., USA), and p<0.05 was considered statistically significant.

The results of counting the number of CD11b- and F4/80-positive cells in the subretinal and retinal portions indicated that the number of inflammatory cells significantly decreased in the group injected with the mTOR shRNA when compared to the groups injected with saline or nonspecific shRNA. The number of F4/80-positive inflammatory cells in the retina was 84.4±17 or 82.8±10.0 upon injection of saline or nonspecific shRNA, but decreased to 42.4±10.4 upon injection of the mTOR shRNA, and the number of CD11b-positive cells decreased from 123.8±13.0 or 127.6±14.4 to 90.0±11.6 (FIG. 4).

This suggests that the inhibition of mTOR by the mTOR shRNA exhibits a therapeutic effect against macular degeneration by reducing the introduction and proliferation of inflammatory cells in the retina.

3-4: Examination of the Activation of Autophagy by mTOR shRNA

Figure 5:
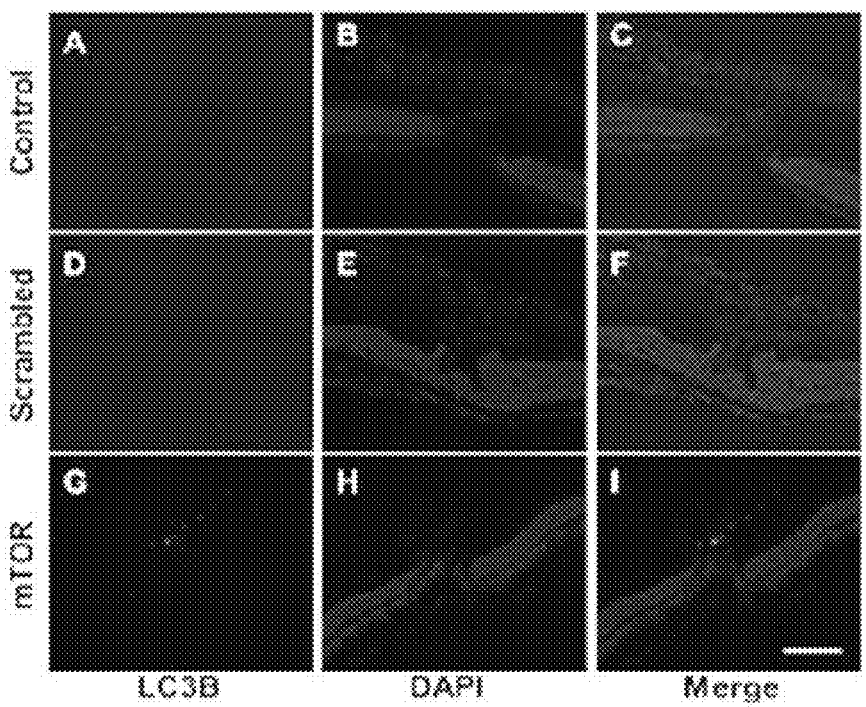
FIG. 5 depicts images showing the results of examining changes in autophagy after administration of shRNA to a laser-induced choroidal neovascularization macular degeneration model wherein (a) shows LC3B-positive cells and (b) shows ATG7-positive cells.
Figure 5:
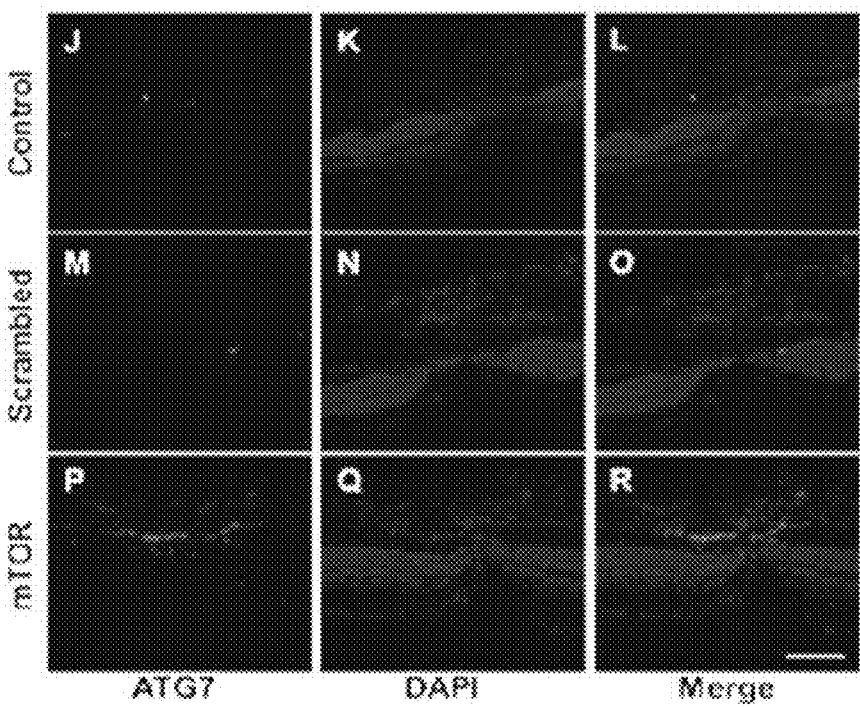

In order to examine whether autophagy is involved in the reduction of choroidal neovascularization lesions by the mTOR shRNA, immunofluorescence staining was performed using the anti-LC3 antibody (1:200; Novus Biologicals, Littleton, Colo., NB110-2220) and anti-ATG7 antibody capable of selectively detecting autophagy. The preparation of tissue samples for immunofluorescence staining followed the process of preparing neural retina-retinal pigment epithelium-choroid complex tissue samples as described in Example 3-2 above. As a result, it was shown that LC3B- or ATG7-positive cells were not observed in the groups injected with saline or nonspecific shRNA, but were observed in the group injected with the mTOR shRNA, indicating that autophagy is activated by the mTOR shRNA (FIG. 5).

This suggests that the inhibition of mTOR by the mTOR shRNA exhibits a therapeutic effect against macular degeneration by activating autophagy.

3-5: Reduction of Apoptosis by mTOR shRNA

In order to examine the effect of the mTOR shRNA on apoptosis in laser-induced choroidal neovascularization, TUNEL (terminal dUTP nick-end labeling) was performed. The preparation of tissue samples for immunofluorescence staining followed the process of preparing neural retina-retinal pigment epithelium-choroid complex tissue samples as described in Example 3-2 above. The results of observation performed 14 days after laser irradiation indicated that, in all the groups treated with saline, nonspecific, and the mTOR shRNA, TUNEL-positive cells were found in the outer nuclear layer (ONL) and the CNV. It was shown that the number of TUNEL-positive cells in the ONL significantly decreased in the group injected with the mTOR shRNA when compared to the groups injected with saline or nonspecific shRNA. Specifically, it was shown that the number of TUNEL-positive cells was 17.8±4.8 or 19.4±4.0 upon injection of saline or nonspecific shRNA, but decreased to 8.4±3.0 upon injection of the mTOR shRNA (FIG. 6).

This suggests that the inhibition of mTOR by the mTOR shRNA exhibits a therapeutic effect against macular degeneration by reducing the number of apoptotic cells located in the outer nuclear layer.

Taken together, as shown in FIGS. 1 and 3, it was confirmed that, in the laser-induced choroidal neovascularization macular degeneration models, the size of the lesion significantly decreased in the mTOR shRNA test group compared to the saline control group and the nonspecific shRNA control group, indicating that the mTOR shRNA has the effect of treating macular degeneration.

In addition, as shown in FIGS. 4 and 6, it was observed that the number of inflammatory cells around the choroidal neovascularization lesion was reduced and apoptosis was also reduced, compared to the two control groups. This suggests that the shRNA-based inhibition of mTOR simply reduces the size of choroidal neovascularization lesions, and also exhibits the effects of alleviating inflammatory responses and inhibiting the apoptosis of neural cells in peripheral neural retinal tissue.

INDUSTRIAL APPLICABILITY

The pharmaceutical composition according to the present invention can effectively treat age-related macular degeneration, a representative retinal disease that causes blindness in adults.

Although the present invention has been described in detail with references to the specific features, it will be apparent to those skilled in the art that this description is only for a preferred embodiment and does not limit the scope of the present invention. Thus, the substantial scope of the present invention will be defined by the appended claims and equivalents thereof.

The invention claimed is:

1. A method for treating age-related macular degeneration, the method comprising administering to a patient a recombinant vector comprising an shRNA (shRNA-mTOR) with the ability to inhibit mTOR and of the nucleotide sequence of SEQ ID NO: 1.

2. The method of claim 1, wherein the recombinant vector is an AAV vector.

* * * * *

SEQUENCE LISTING

```
<160> NUMBER OF SEQ ID NOS: 1

<210> SEQ ID NO 1
<211> LENGTH: 19
<212> TYPE: RNA
<213> ORGANISM: Artificial Sequence
<220> FEATURE:
<223> OTHER INFORMATION: shRNA mTOR

<400> SEQUENCE: 1
gaauguugac caaugcuau                                              19
```